United States Patent
Zdeblick

(10) Patent No.: US 9,941,931 B2
(45) Date of Patent: *Apr. 10, 2018

(54) SYSTEM FOR SUPPLY CHAIN MANAGEMENT

(71) Applicant: Proteus Digital Health, Inc., Redwood City, CA (US)

(72) Inventor: Mark J. Zdeblick, Portola Valley, CA (US)

(73) Assignee: PROTEUS DIGITAL HEALTH, INC., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/491,226

(22) Filed: Sep. 19, 2014

(65) Prior Publication Data

US 2015/0171924 A1 Jun. 18, 2015

Related U.S. Application Data

(63) Continuation of application No. 13/508,327, filed as application No. PCT/US2010/055522 on Nov. 4, 2010, now Pat. No. 8,868,453.

(Continued)

(51) Int. Cl.
*G06Q 40/00* (2012.01)
*H04B 5/00* (2006.01)
(Continued)

(52) U.S. Cl.
CPC .............. *H04B 5/0012* (2013.01); *G06K 7/01* (2013.01); *G06Q 10/06* (2013.01)

(58) Field of Classification Search
None
See application file for complete search history.

(56) References Cited

U.S. PATENT DOCUMENTS 3,345,989 A 10/1967 Reynolds
3,409,721 A 11/1968 Applezweig
(Continued)

FOREIGN PATENT DOCUMENTS

CA 2953847 11/2006
CN 2748032 12/2005
(Continued)

OTHER PUBLICATIONS

Ferguson et al., "Wireless communication with implanted medical devices using the conductive properties of the body," Expert Rev Med Devices, Jul. 2011, 8(4): 427-433.

(Continued)

*Primary Examiner* — Shay S Glass
(74) *Attorney, Agent, or Firm* — K&L Gates LLP

(57) ABSTRACT

A system for tracking a product from origin to destination is disclosed. The system includes a probe that comprises two plates, a power source and a processor. The power source is controlled by the processor to produce an oscillating output at the plates. Using the oscillating voltage, the probe interrogates a device through capacitive coupling. The device includes a control unit, a memory unit, and first and second materials physically associated with the device for communication using capacitive coupling. Information associated with the device is transferred from the device to the probe through capacitive coupling between the first and second materials and the first and second plates, respectively.

19 Claims, 9 Drawing Sheets

Related U.S. Application Data

(60) Provisional application No. 61/258,182, filed on Nov. 4, 2009.

(51) Int. Cl.
*G06Q 10/06* (2012.01)
*G06K 7/01* (2006.01)

(56) References Cited

U.S. PATENT DOCUMENTS

| | | |
|---|---|---|
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |

(56) References Cited

U.S. PATENT DOCUMENTS

| | | |
|---|---|---|
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,076,437 B1 | 7/2006 | Levy |
| 7,081,693 B2 | 7/2006 | Hamel et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |

(56) References Cited

U.S. PATENT DOCUMENTS

| | | | |
|---|---|---|---|
| 7,291,497 | B2 | 11/2007 | Holmes |
| 7,292,139 | B2 | 11/2007 | Mazar et al. |
| 7,294,105 | B1 | 11/2007 | Islam |
| 7,295,877 | B2 | 11/2007 | Govari |
| 7,311,665 | B2 | 12/2007 | Hawthorne |
| 7,313,163 | B2 | 12/2007 | Liu |
| 7,317,378 | B2 | 1/2008 | Jarvis et al. |
| 7,318,808 | B2 | 1/2008 | Tarassenko et al. |
| 7,336,732 | B1 | 2/2008 | Wiss |
| 7,336,929 | B2 | 2/2008 | Yasuda |
| 7,342,895 | B2 | 3/2008 | Serpa |
| 7,346,380 | B2 | 3/2008 | Axelgaard et al. |
| 7,349,722 | B2 | 3/2008 | Witkowski et al. |
| 7,352,998 | B2 | 4/2008 | Palin |
| 7,353,258 | B2 | 4/2008 | Washburn |
| 7,357,891 | B2 | 4/2008 | Yang et al. |
| 7,359,674 | B2 | 4/2008 | Markki |
| 7,366,558 | B2 | 4/2008 | Virtanen et al. |
| 7,366,675 | B1 | 4/2008 | Walker et al. |
| 7,368,190 | B2 | 5/2008 | Heller et al. |
| 7,368,191 | B2 | 5/2008 | Andelman et al. |
| 7,373,196 | B2 | 5/2008 | Ryu et al. |
| 7,375,739 | B2 | 5/2008 | Robbins |
| 7,376,435 | B2 | 5/2008 | McGowan |
| 7,382,247 | B2 | 6/2008 | Welch et al. |
| 7,382,263 | B2 | 6/2008 | Danowski et al. |
| 7,387,607 | B2 | 6/2008 | Holt |
| 7,388,903 | B2 | 6/2008 | Godfrey et al. |
| 7,389,088 | B2 | 6/2008 | Kim |
| 7,392,015 | B1 | 6/2008 | Farlow |
| 7,395,106 | B2 | 7/2008 | Ryu et al. |
| 7,396,330 | B2 | 7/2008 | Banet |
| 7,404,968 | B2 | 7/2008 | Abrams et al. |
| 7,413,544 | B2 | 8/2008 | Kerr |
| 7,414,534 | B1 | 8/2008 | Kroll et al. |
| 7,414,543 | B2 | 8/2008 | Rye et al. |
| 7,415,242 | B1 | 8/2008 | Ngan |
| 7,419,468 | B2 | 9/2008 | Shimizu et al. |
| 7,424,268 | B2 | 9/2008 | Diener |
| 7,424,319 | B2 | 9/2008 | Muehlsteff |
| 7,427,266 | B2 | 9/2008 | Ayer et al. |
| 7,433,731 | B2 | 10/2008 | Matsumura et al. |
| 7,471,665 | B2 | 12/2008 | Perlman |
| 7,485,093 | B2 | 2/2009 | Glukhovsky |
| 7,485,095 | B2 | 2/2009 | Shusterman |
| 7,499,674 | B2 | 3/2009 | Salokannel |
| 7,502,643 | B2 | 3/2009 | Farringdon et al. |
| 7,505,795 | B1 | 3/2009 | Lim et al. |
| 7,508,248 | B2 | 3/2009 | Yoshida |
| 7,510,121 | B2 | 3/2009 | Koenck |
| 7,512,448 | B2 | 3/2009 | Malick |
| 7,512,860 | B2 | 3/2009 | Miyazaki et al. |
| 7,515,043 | B2 | 4/2009 | Welch |
| 7,519,416 | B2 | 4/2009 | Sula et al. |
| 7,523,756 | B2 | 4/2009 | Minai |
| 7,525,426 | B2 | 4/2009 | Edelstein |
| 7,539,533 | B2 | 5/2009 | Tran |
| 7,542,878 | B2 | 6/2009 | Nanikashvili |
| 7,547,278 | B2 | 6/2009 | Miyazaki et al. |
| 7,551,590 | B2 | 6/2009 | Haller |
| 7,554,452 | B2 | 6/2009 | Cole |
| 7,558,620 | B2 | 7/2009 | Ishibashi |
| 7,558,965 | B2 | 7/2009 | Wheeler et al. |
| 7,575,005 | B2 | 8/2009 | Mumford |
| 7,616,111 | B2 | 11/2009 | Covannon |
| 7,616,710 | B2 | 11/2009 | Kim et al. |
| 7,617,001 | B2 | 11/2009 | Penner et al. |
| 7,639,473 | B2 | 12/2009 | Hsu et al. |
| 7,640,802 | B2 | 1/2010 | King et al. |
| 7,647,112 | B2 | 1/2010 | Tracey |
| 7,647,185 | B2 | 1/2010 | Tarassenko et al. |
| 7,653,031 | B2 | 1/2010 | Godfrey et al. |
| 7,668,437 | B1 | 2/2010 | Yamada et al. |
| 7,672,703 | B2 | 3/2010 | Yeo et al. |
| 7,672,714 | B2 | 3/2010 | Kuo |
| 7,673,679 | B2 | 3/2010 | Harrison et al. |
| 7,678,043 | B2 | 3/2010 | Gilad |
| 7,689,437 | B1 | 3/2010 | Teller et al. |
| 7,689,833 | B2 | 3/2010 | Lange |
| 7,697,994 | B2 | 4/2010 | VanDanacker et al. |
| 7,712,288 | B2 | 5/2010 | Ramasubramanian et al. |
| 7,720,036 | B2 | 5/2010 | Sadri |
| 7,729,776 | B2 | 6/2010 | Von Arx et al. |
| 7,733,224 | B2 | 6/2010 | Tran |
| 7,736,318 | B2 | 6/2010 | Cosentino |
| 7,747,454 | B2 | 6/2010 | Bartfeld et al. |
| 7,756,587 | B2 | 7/2010 | Penner et al. |
| 7,764,996 | B2 | 7/2010 | Zhang et al. |
| 7,779,614 | B1 | 8/2010 | McGonagle et al. |
| 7,796,043 | B2 | 9/2010 | Euliano et al. |
| 7,797,033 | B2 | 9/2010 | D'Andrea et al. |
| 7,806,852 | B1 | 10/2010 | Jursen |
| 7,809,399 | B2 | 10/2010 | Lu |
| 7,844,341 | B2 | 11/2010 | Von Arx et al. |
| 7,857,766 | B2 | 12/2010 | Lasater et al. |
| 7,860,731 | B2 | 12/2010 | Jackson et al. |
| 7,899,526 | B2 | 3/2011 | Benditt et al. |
| 7,904,133 | B2 | 3/2011 | Gehman et al. |
| D639,437 | S | 6/2011 | Bishay et al. |
| 7,978,064 | B2 | 7/2011 | Zdeblick et al. |
| 8,025,149 | B2 | 9/2011 | Sterry et al. |
| 8,036,731 | B2 | 10/2011 | Kimchy et al. |
| 8,036,748 | B2 | 10/2011 | Zdeblick et al. |
| 8,060,249 | B2 | 11/2011 | Bear et al. |
| 8,073,707 | B2 | 12/2011 | Teller et al. |
| 8,083,128 | B2 | 12/2011 | Dembo et al. |
| 8,123,576 | B2 | 2/2012 | Kim |
| 8,135,596 | B2 | 3/2012 | Jung et al. |
| 8,180,425 | B2 | 5/2012 | Selvitelli et al. |
| 8,185,191 | B1 | 5/2012 | Shapiro et al. |
| 8,185,646 | B2 | 5/2012 | Headley |
| 8,200,320 | B2 | 6/2012 | Kovacs |
| 8,209,018 | B2 | 6/2012 | Osorio et al. |
| 8,214,007 | B2 | 7/2012 | Baker et al. |
| 8,224,667 | B1 | 7/2012 | Miller et al. |
| 8,238,998 | B2 | 8/2012 | Park |
| 8,249,686 | B2 | 8/2012 | Libbus et al. |
| 8,253,586 | B1 | 8/2012 | Matak |
| 8,254,853 | B2 | 8/2012 | Rofougaran |
| 8,258,962 | B2 | 9/2012 | Robertson et al. |
| 8,262,394 | B2 | 9/2012 | Walker et al. |
| 8,271,106 | B2 | 9/2012 | Wehba et al. |
| 8,285,356 | B2 | 10/2012 | Bly et al. |
| 8,290,574 | B2 | 10/2012 | Feild et al. |
| 8,301,232 | B2 | 10/2012 | Albert et al. |
| 8,308,640 | B2 | 11/2012 | Baldus et al. |
| 8,314,619 | B2 | 11/2012 | Takiguchi |
| 8,315,687 | B2 | 11/2012 | Cross et al. |
| 8,343,068 | B2 | 1/2013 | Najafi et al. |
| 8,369,936 | B2 | 2/2013 | Farringdon et al. |
| 8,386,009 | B2 | 2/2013 | Lindberg et al. |
| 8,389,003 | B2 | 3/2013 | Mintchev et al. |
| 8,404,275 | B2 | 3/2013 | Habboushe |
| 8,440,274 | B2 | 5/2013 | Wang |
| 8,454,528 | B2 | 6/2013 | Yuen et al. |
| 8,454,561 | B2 | 6/2013 | Uber, III et al. |
| 8,514,086 | B2 | 8/2013 | Harper et al. |
| 8,542,123 | B2 | 9/2013 | Robertson |
| 8,564,432 | B2 | 10/2013 | Covannon et al. |
| 8,564,627 | B2 | 10/2013 | Suzuki et al. |
| 8,583,227 | B2 | 11/2013 | Savage et al. |
| 8,597,186 | B2 | 12/2013 | Hafezi et al. |
| 8,634,838 | B2 | 1/2014 | Hellwig et al. |
| 8,660,645 | B2 | 2/2014 | Stevenson et al. |
| 8,668,280 | B2 | 3/2014 | Heller et al. |
| 8,668,643 | B2 | 3/2014 | Kinast |
| 8,718,193 | B2 | 5/2014 | Arne et al. |
| 8,722,085 | B2 | 5/2014 | McKinney et al. |
| 8,762,733 | B2 | 6/2014 | Derchak et al. |
| 8,771,183 | B2 | 7/2014 | Sloan |
| 8,810,260 | B1 | 8/2014 | Zhou |
| 8,823,510 | B2 | 9/2014 | Downey et al. |
| 8,836,513 | B2 | 9/2014 | Hafezi et al. |
| 8,838,217 | B2 | 9/2014 | Myr |

(56) References Cited

U.S. PATENT DOCUMENTS

| | | | |
|---|---|---|---|
| 8,868,453 B2 * | 10/2014 | Zdeblick | G06Q 10/06 705/28 |
| 8,908,943 B2 | 12/2014 | Berry et al. | |
| 8,926,509 B2 | 1/2015 | Magar et al. | |
| 8,932,221 B2 | 1/2015 | Colliou et al. | |
| 8,945,005 B2 | 2/2015 | Hafezi et al. | |
| 8,956,287 B2 | 2/2015 | Zdeblick et al. | |
| 8,956,288 B2 | 2/2015 | Hafezi et al. | |
| 8,966,973 B1 | 3/2015 | Milone | |
| 8,989,837 B2 | 3/2015 | Weinstein et al. | |
| 9,031,658 B2 | 5/2015 | Chiao et al. | |
| 9,047,746 B1 | 6/2015 | Euliano et al. | |
| 9,060,708 B2 | 6/2015 | Robertson et al. | |
| 9,125,868 B2 | 9/2015 | McKinney et al. | |
| 9,189,941 B2 | 11/2015 | Eschelman et al. | |
| 9,226,663 B2 | 1/2016 | Fei | |
| 9,226,679 B2 | 1/2016 | Balda | |
| 9,235,683 B2 | 1/2016 | Robertson et al. | |
| 9,258,035 B2 | 2/2016 | Robertson et al. | |
| 9,270,025 B2 | 2/2016 | Robertson et al. | |
| 9,277,864 B2 | 3/2016 | Yang et al. | |
| 9,278,177 B2 | 3/2016 | Edwards et al. | |
| 9,433,371 B2 | 9/2016 | Hafezi et al. | |
| 9,439,582 B2 | 9/2016 | Berkman et al. | |
| 9,439,599 B2 | 9/2016 | Thompson et al. | |
| 9,444,503 B2 | 9/2016 | Arne et al. | |
| 9,517,012 B2 | 12/2016 | Lane et al. | |
| 9,603,550 B2 | 3/2017 | Behzadi | |
| 2001/0027331 A1 | 10/2001 | Thompson | |
| 2001/0031071 A1 | 10/2001 | Nichols et al. | |
| 2001/0039503 A1 | 11/2001 | Chan et al. | |
| 2001/0044588 A1 | 11/2001 | Mault | |
| 2001/0051766 A1 | 12/2001 | Gazdinski | |
| 2001/0056262 A1 | 12/2001 | Cabiri et al. | |
| 2002/0002326 A1 | 1/2002 | Causey et al. | |
| 2002/0019586 A1 | 2/2002 | Teller et al. | |
| 2002/0026111 A1 | 2/2002 | Ackerman | |
| 2002/0032384 A1 | 3/2002 | Raymond et al. | |
| 2002/0032385 A1 | 3/2002 | Raymond et al. | |
| 2002/0040278 A1 | 4/2002 | Anuzis et al. | |
| 2002/0067270 A1 | 6/2002 | Yarin et al. | |
| 2002/0077620 A1 | 6/2002 | Sweeney et al. | |
| 2002/0132226 A1 | 9/2002 | Nair | |
| 2002/0138009 A1 | 9/2002 | Brockway et al. | |
| 2002/0184415 A1 | 12/2002 | Naghavi et al. | |
| 2002/0192159 A1 | 12/2002 | Reitberg | |
| 2002/0193669 A1 | 12/2002 | Glukhovsky | |
| 2002/0193846 A1 | 12/2002 | Pool et al. | |
| 2002/0198470 A1 | 12/2002 | Imran et al. | |
| 2003/0017826 A1 | 1/2003 | Fishman | |
| 2003/0023150 A1 | 1/2003 | Yokoi et al. | |
| 2003/0028226 A1 | 2/2003 | Thompson | |
| 2003/0037063 A1 | 2/2003 | Schwartz | |
| 2003/0063522 A1 | 4/2003 | Sagar | |
| 2003/0065536 A1 | 4/2003 | Hansen | |
| 2003/0076179 A1 | 4/2003 | Branch et al. | |
| 2003/0083559 A1 | 5/2003 | Thompson | |
| 2003/0126593 A1 | 7/2003 | Mault | |
| 2003/0130714 A1 | 7/2003 | Nielsen et al. | |
| 2003/0135128 A1 | 7/2003 | Suffin et al. | |
| 2003/0135392 A1 | 7/2003 | Vrijens et al. | |
| 2003/0152622 A1 | 8/2003 | Louie-Helm et al. | |
| 2003/0158466 A1 | 8/2003 | Lynn et al. | |
| 2003/0158756 A1 | 8/2003 | Abramson | |
| 2003/0162556 A1 | 8/2003 | Libes | |
| 2003/0164401 A1 | 9/2003 | Andreasson et al. | |
| 2003/0167000 A1 | 9/2003 | Mullick et al. | |
| 2003/0171791 A1 | 9/2003 | KenKnight | |
| 2003/0171898 A1 | 9/2003 | Tarassenko et al. | |
| 2003/0181788 A1 | 9/2003 | Yokoi et al. | |
| 2003/0181815 A1 | 9/2003 | Ebner et al. | |
| 2003/0185286 A1 | 10/2003 | Yuen | |
| 2003/0187337 A1 | 10/2003 | Tarassenko et al. | |
| 2003/0187338 A1 | 10/2003 | Say et al. | |
| 2003/0195403 A1 | 10/2003 | Berner et al. | |
| 2003/0198619 A1 | 10/2003 | Dong et al. | |
| 2003/0213495 A1 | 11/2003 | Fujita et al. | |
| 2003/0214579 A1 | 11/2003 | Iddan | |
| 2003/0216622 A1 | 11/2003 | Meron et al. | |
| 2003/0216625 A1 | 11/2003 | Phipps | |
| 2003/0216666 A1 | 11/2003 | Ericson et al. | |
| 2003/0216729 A1 | 11/2003 | Marchitto | |
| 2003/0216793 A1 | 11/2003 | Karlsson et al. | |
| 2003/0229382 A1 | 12/2003 | Sun et al. | |
| 2003/0232895 A1 | 12/2003 | Omidian et al. | |
| 2004/0008123 A1 | 1/2004 | Carrender et al. | |
| 2004/0018476 A1 | 1/2004 | LaDue | |
| 2004/0019172 A1 | 1/2004 | Yang et al. | |
| 2004/0034295 A1 | 2/2004 | Salganicoff | |
| 2004/0049245 A1 | 3/2004 | Gass | |
| 2004/0073095 A1 | 4/2004 | Causey et al. | |
| 2004/0073454 A1 | 4/2004 | Urquhart et al. | |
| 2004/0077995 A1 | 4/2004 | Ferek-Petric | |
| 2004/0082982 A1 | 4/2004 | Gord et al. | |
| 2004/0087839 A1 | 5/2004 | Raymond et al. | |
| 2004/0092801 A1 | 5/2004 | Drakulic | |
| 2004/0106859 A1 | 6/2004 | Say et al. | |
| 2004/0111011 A1 | 6/2004 | Uchiyama et al. | |
| 2004/0115507 A1 | 6/2004 | Potter et al. | |
| 2004/0115517 A1 | 6/2004 | Fukada et al. | |
| 2004/0121015 A1 | 6/2004 | Chidlaw et al. | |
| 2004/0122296 A1 | 6/2004 | Hatlestad | |
| 2004/0122297 A1 | 6/2004 | Stahmann et al. | |
| 2004/0138558 A1 | 7/2004 | Dunki-Jacobs et al. | |
| 2004/0147326 A1 | 7/2004 | Stiles | |
| 2004/0148140 A1 | 7/2004 | Tarassenko et al. | |
| 2004/0153007 A1 | 8/2004 | Harris | |
| 2004/0167226 A1 | 8/2004 | Serafini | |
| 2004/0167801 A1 | 8/2004 | Say et al. | |
| 2004/0171914 A1 | 9/2004 | Avni | |
| 2004/0193020 A1 | 9/2004 | Chiba | |
| 2004/0193029 A1 | 9/2004 | Gluhovsky | |
| 2004/0193446 A1 | 9/2004 | Mayer et al. | |
| 2004/0199222 A1 | 10/2004 | Sun et al. | |
| 2004/0215084 A1 | 10/2004 | Shimizu et al. | |
| 2004/0218683 A1 | 11/2004 | Batra | |
| 2004/0220643 A1 | 11/2004 | Schmidt | |
| 2004/0224644 A1 | 11/2004 | Wu | |
| 2004/0225199 A1 | 11/2004 | Evanyk | |
| 2004/0253304 A1 | 12/2004 | Gross et al. | |
| 2004/0258571 A1 | 12/2004 | Lee et al. | |
| 2004/0260154 A1 | 12/2004 | Sidelnik | |
| 2004/0267240 A1 | 12/2004 | Gross et al. | |
| 2005/0017841 A1 | 1/2005 | Doi | |
| 2005/0020887 A1 | 1/2005 | Goldberg | |
| 2005/0021103 A1 | 1/2005 | DiLorenzo | |
| 2005/0021370 A1 | 1/2005 | Riff | |
| 2005/0021372 A1 | 1/2005 | Mikkelsen | |
| 2005/0024198 A1 | 2/2005 | Ward | |
| 2005/0027175 A1 | 2/2005 | Yang | |
| 2005/0027205 A1 | 2/2005 | Tarassenko et al. | |
| 2005/0038321 A1 | 2/2005 | Fujita et al. | |
| 2005/0043634 A1 | 2/2005 | Yokoi et al. | |
| 2005/0043894 A1 | 2/2005 | Fernandez | |
| 2005/0054897 A1 | 3/2005 | Hashimoto et al. | |
| 2005/0055014 A1 | 3/2005 | Coppeta et al. | |
| 2005/0062644 A1 | 3/2005 | Leci | |
| 2005/0065407 A1 | 3/2005 | Nakamura et al. | |
| 2005/0070778 A1 | 3/2005 | Lackey | |
| 2005/0075145 A1 | 4/2005 | Dvorak et al. | |
| 2005/0090753 A1 | 4/2005 | Goor et al. | |
| 2005/0092108 A1 | 5/2005 | Andermo | |
| 2005/0096514 A1 | 5/2005 | Starkebaum | |
| 2005/0096562 A1 | 5/2005 | Delalic et al. | |
| 2005/0101843 A1 | 5/2005 | Quinn | |
| 2005/0101872 A1 | 5/2005 | Sattler | |
| 2005/0115561 A1 | 6/2005 | Stahmann et al. | |
| 2005/0116820 A1 | 6/2005 | Goldreich | |
| 2005/0117389 A1 | 6/2005 | Worledge | |
| 2005/0121322 A1 | 6/2005 | Say et al. | |
| 2005/0131281 A1 | 6/2005 | Ayer et al. | |
| 2005/0137480 A1 | 6/2005 | Alt et al. | |
| 2005/0143623 A1 | 6/2005 | Kojima | |
| 2005/0146594 A1 | 7/2005 | Nakatani et al. | |

(56) References Cited

U.S. PATENT DOCUMENTS

| | | |
|---|---|---|
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowski |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |

(56) References Cited

U.S. PATENT DOCUMENTS

| | | |
|---|---|---|
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |

(56) References Cited

U.S. PATENT DOCUMENTS

| | | |
|---|---|---|
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0185055 A1 | 7/2010 | Robertson et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelsen et al. |
| 2012/0265544 A1 | 10/2012 | Hwang et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0171596 A1 | 7/2013 | French |
| 2013/0185228 A1 | 7/2013 | Dresner |
| 2013/0196012 A1 | 8/2013 | Dill |
| 2014/0039445 A1 | 2/2014 | Austin et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0334575 A1 | 11/2014 | Arne et al. |
| 2014/0349256 A1 | 11/2014 | Connor |
| 2014/0374276 A1 | 12/2014 | Guthrie et al. |
| 2015/0051465 A1 | 2/2015 | Robertson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0165313 A1 | 6/2015 | Thompson et al. |
| 2015/0182463 A1 | 7/2015 | Hafezi et al. |

(56) References Cited

U.S. PATENT DOCUMENTS

| | | | |
|---|---|---|---|
| 2015/0193593 | A1 | 7/2015 | Zdeblick et al. |
| 2015/0230728 | A1 | 8/2015 | Hafezi et al. |
| 2016/0106339 | A1 | 4/2016 | Behzadi et al. |
| 2016/0155316 | A1 | 6/2016 | Hafezi et al. |
| 2017/0000180 | A1 | 1/2017 | Arne et al. |
| 2017/0215761 | A1 | 8/2017 | Zdeblick |
| 2017/0270779 | A1 | 9/2017 | Zdeblick et al. |
| 2017/0290513 | A1 | 10/2017 | O'Reilly et al. |

FOREIGN PATENT DOCUMENTS

| | | |
|---|---|---|
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | 2000-506410 | 5/1912 |
| JP | 6117949 | 1/1986 |
| JP | S63280393 | 11/1988 |
| JP | H01285247 | 11/1989 |
| JP | 05-228128 | 9/1993 |
| JP | H0884779 | 4/1996 |
| JP | 09-330159 | 12/1997 |
| JP | 10-14898 | 1/1998 |
| JP | H11195415 | 7/1999 |
| JP | 2001078974 | 3/2001 |
| JP | 2002-224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 3454525 | 10/2003 |
| JP | 2003325440 | 11/2003 |
| JP | 2004-7187 | 1/2004 |
| JP | 2004507188 | 3/2004 |
| JP | 2004-134384 | 4/2004 |
| JP | 2004-313242 | 11/2004 |
| JP | 2004318534 | 11/2004 |
| JP | 2004364016 | 12/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005148021 | 6/2005 |
| JP | 2005152037 | 6/2005 |
| JP | 2005287691 | 10/2005 |
| JP | 2005-532841 | 11/2005 |
| JP | 2005-532849 | 11/2005 |
| JP | 2005343515 | 12/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007-159631 | 6/2007 |
| JP | 2007151809 | 6/2007 |
| JP | 2007-313340 | 12/2007 |
| JP | 2007-330677 | 12/2007 |
| JP | 2008011865 | 1/2008 |
| JP | 2008501415 | 1/2008 |
| JP | 2008191955 | 8/2008 |
| JP | 2008289724 | 12/2008 |
| JP | 2009034345 | 2/2009 |
| JP | 2009-061236 | 3/2009 |
| JP | 2009030541 | 3/2009 |
| JP | 2011519583 | 7/2011 |
| KR | 20020015907 | 3/2002 |
| KR | 20020061744 | 7/2002 |
| KR | 200600977523 | 7/2006 |
| KR | 927471 | 11/2009 |
| KR | 20110137001 | 12/2011 |
| KR | 10-2012-09995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9516393 | 6/1995 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | WO0147466 | 7/2001 |
| WO | WO0149364 | 7/2001 |
| WO | WO0174011 | 10/2001 |
| WO | WO0180731 | 11/2001 |
| WO | WO0235997 | 5/2002 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |

(56) References Cited

FOREIGN PATENT DOCUMENTS

| | | |
|---|---|---|
| WO | WO2006075016 | 7/2006 |
| WO | WO2006100620 | 9/2006 |
| WO | WO2006109072 | 10/2006 |
| WO | WO2006/123346 | 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | WO2015112603 | 7/2015 |

OTHER PUBLICATIONS

Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.

Greene, "Medicaid Efforts to Incentivize Healthy Behaviours", Center for Health Care Strategies, Inc., Resource Paper, Jul. 2007.

Sharma, et al., "The Future is Wireless: Advances in Wireless Diagnostic and Therapeutic Technologies in Gastoenterology," Gastroenterology, Elesevier, Philadelphia, PA, vol. 137, No. 2, Aug. 1, 2009, pp. 434-439.

AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.

Arshak et al., A Review and Adaptation of Methods of Object Tracking to Telemetry Capsules IC-Med; Jan. 2007 vol. 1, No. 1, Issue 1, 12pp.

"ASGE Technology Status Evaluation Report: wireless capsule endoscopy" American Soc. For Gastrointestinal Endoscopy; Apr. 2006 vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; Sep. 2003; Abstract Only.

Barrie, Heidelberg pH capsule gastric analysis. Texbook of Natural Medicine, (1992), Pizzorno, Murray & Barrie.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory", Current Separations, 18:3 (1999) p. 91-96.

Delvaux et al., "Capsule endoscopy: Technique and indications" Clinical Gastoenterology; Oct. 2008 vol. 22, Issue 5, 1pp. (Abstract Only).

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Evanczuk, S., "PIC MCU software library uses human body for secure communications link" ; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.

Fawaz et al., "Enhanced Telemetry System using CP-QPSK Band-Pass Modulation Technique Suitable for Smart Pill Medical Appli-

(56) References Cited

OTHER PUBLICATIONS cation" IFIP IEEE Dubai Conference Apr. 2008; http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, Or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012; 2 pp.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; MICROSENS S.A. pdf document. First cited by Examiner in Office Action dated Jun. 13, 2011 for U.S. Appl. No. 12/238,345; 4pp.
Jimbo et al., "Gastric-fluid-utilized micro battery for micro medical devices" The Sixth International Workshop on Micro and Nano-technology for Power Genearntion and Energy Conservation Applications, (2006) pp. 97-100.
Jung, S. "Dissolvable 'Transient Electronics' Will Be Good For Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.

Lin et al., "Do Physiological Data Relate to Traditional Usability Indexes?" Proceedings of OZCHI 2005, Canberra, Australia (2005) 10 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Mckenzie et al., "Validation of a new telemetric core temperature monitor" J. Therm. Biol. (2004) 29(7-8):605-11.
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. 2010 http://www.medtronicdiabetes.com/products/index.html; 2 pp.
Medtronic, "Mini Med Paradigm® Revel™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget; Jul. 2008; http://www.engadget.com/2008/07/29/walkers-swallow-rfid-pills-for-science/.
MiniMitter Co. Inc. "Actiheart" Traditional 510(k) Summary. Sep. 27, 2005.
MiniMitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
MiniMitter Co. Inc. VitalSense Integrated Physiological Monitoring System. Product Description. Jul. 2005.
MiniMitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
Radio Antennae, http://www.erikdeman.de/html/sail018h.htm; (2008) 5 pages.
"RFID "pill" monitors marchers" RFID News; Jul. 2008 http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.

(56) References Cited

OTHER PUBLICATIONS

Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics—Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. Aug. 2009.
"The SmartPill Wireless Motility Capsule" SmartPill, The Measure of GI Health; May 2010 http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
TRUTAG, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.
Walkey, "MOSFET Structure and Processing"; 97.398 Physical Electronics Lecture 20.
Watson, et al., "Determination of the relationship between the pH and conductivity of gastric juice" Physiol Meas. 17 (1996) pp. 21-27.
Whipple, Fred L.; "Endoradiosonde," Nature, Jun. 1957, 1239-1240.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
Au-Yeung, K., et al., "A Networked System for Self-Management of Drug Therapy and Wellness", Wireless Health '10, Oct. 5-7, 2010, San Diego, 9 pages.
Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Zhang, Y-T. et al., "Wireless Biomedical Sensing," Wiley Encyclopedia of Biomedical Engineering, 2006, pp. 1-9.
Aronson, J., "Meyer's Side Effects of Cardiovascular Drugs," Elsevier, Mar. 2, 2009, Medical, 840 pages. (Not Attached).
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
McDermott-Wells, P., "What is Bluetooth?", IEEE Potentials, IEEE, New York, NY, vol. 23, No. 5, Dec. 1, 2004, pp. 33-35.
Sammoura, F. et al., "Water-activated disposable and long shelf life microbatteries", Sensors and Actuators A 111 (2004) 79-86.
vonStetten, F. et al., "Biofuel cells as power generation for implantable devices", Pore. Eurosensors XX, (2006), pp. 22-225.

\* cited by examiner

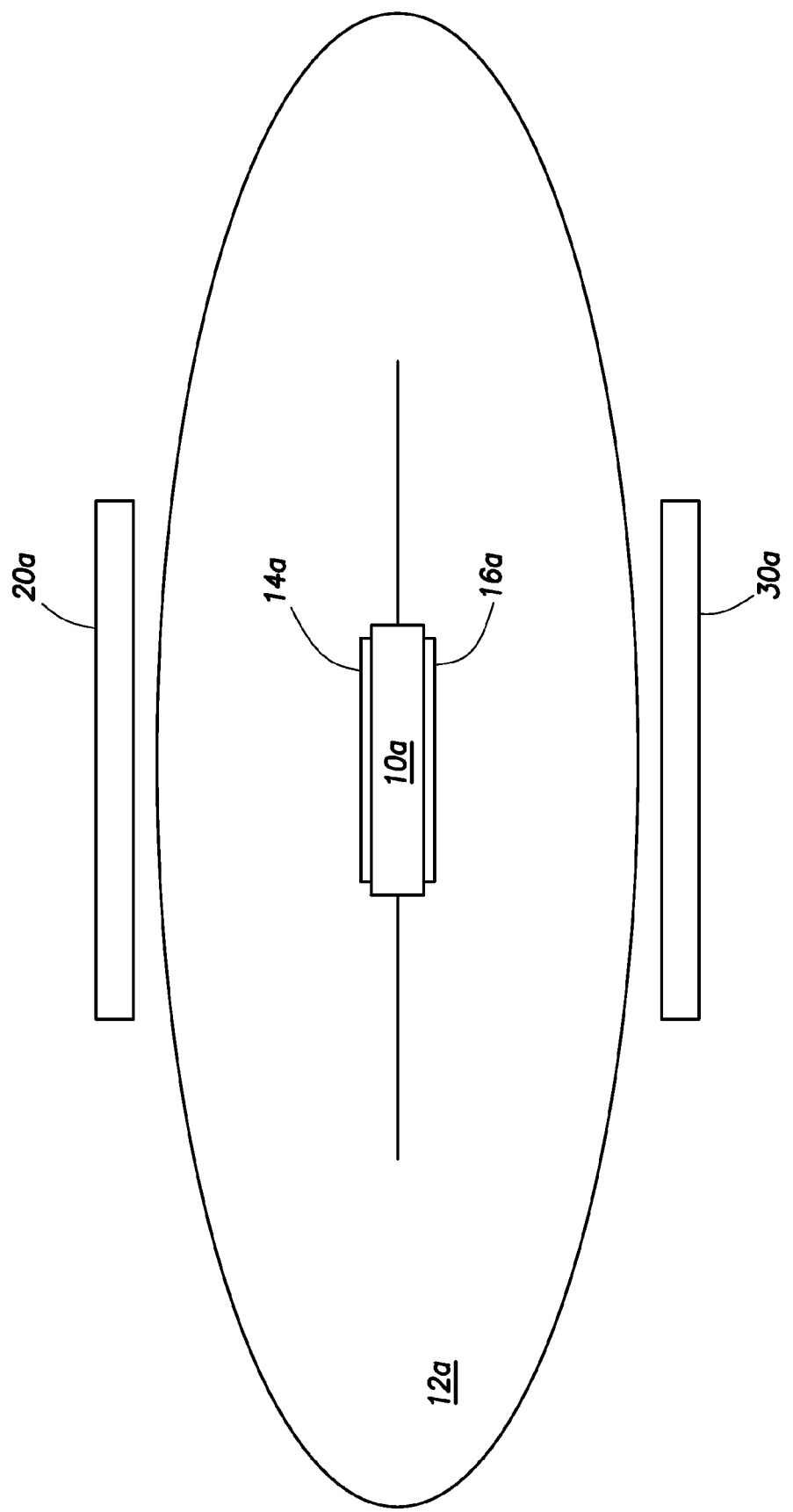

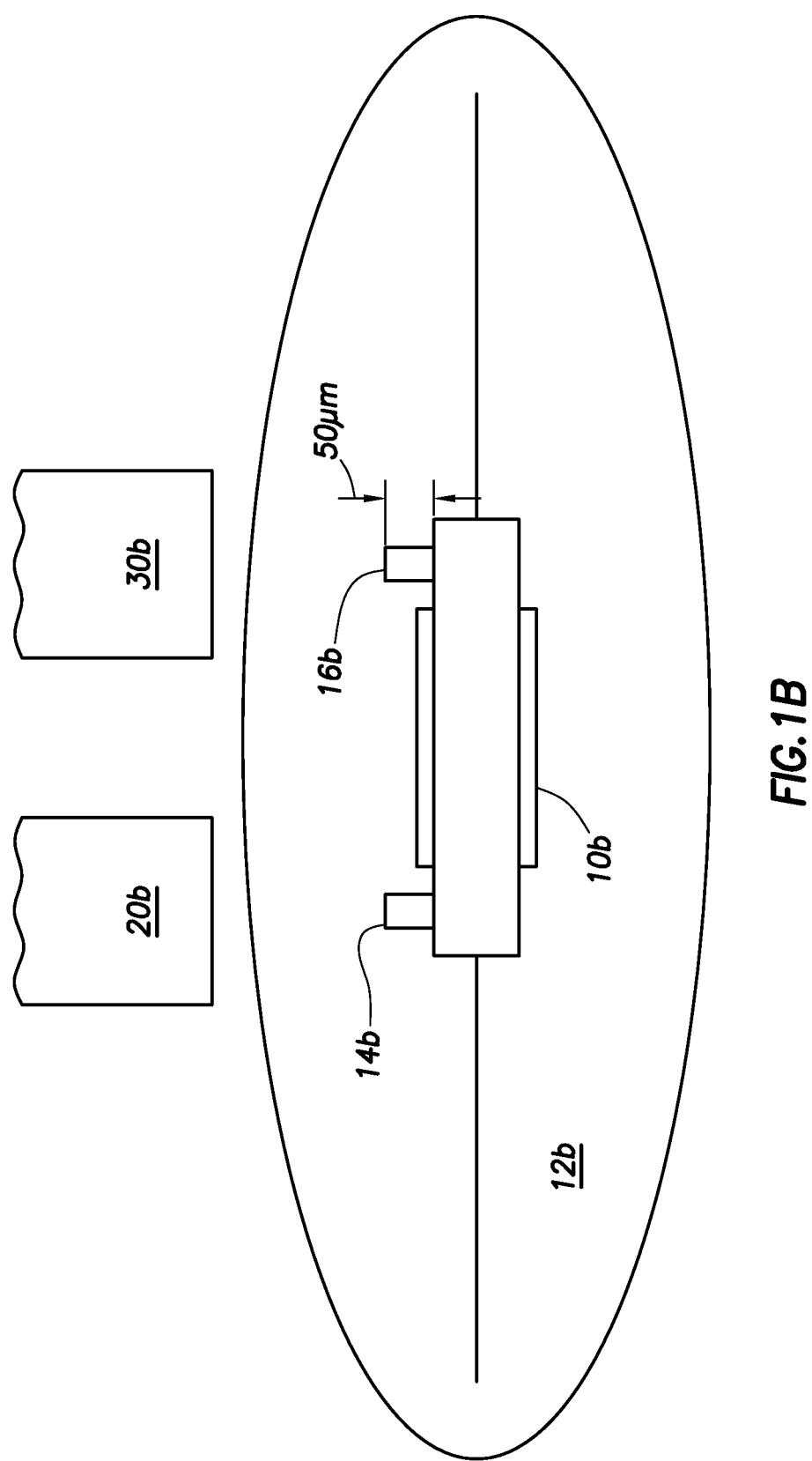

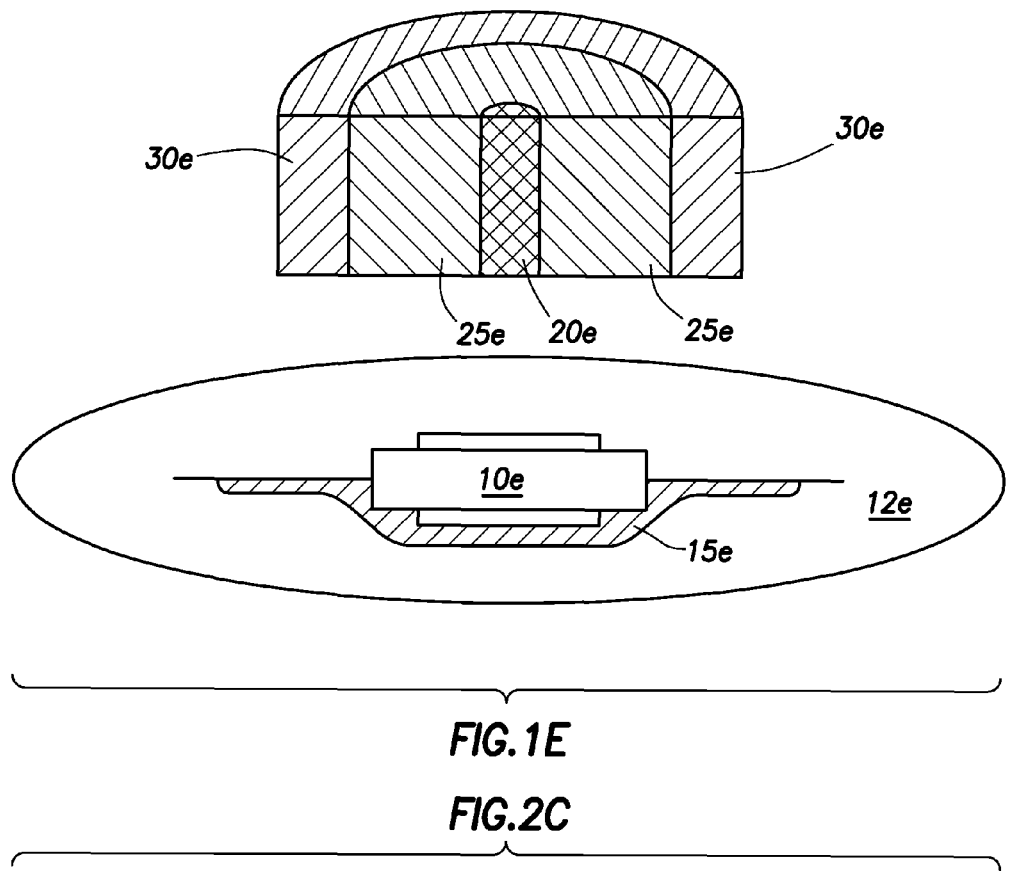
*FIG.1E*
*FIG.2C*
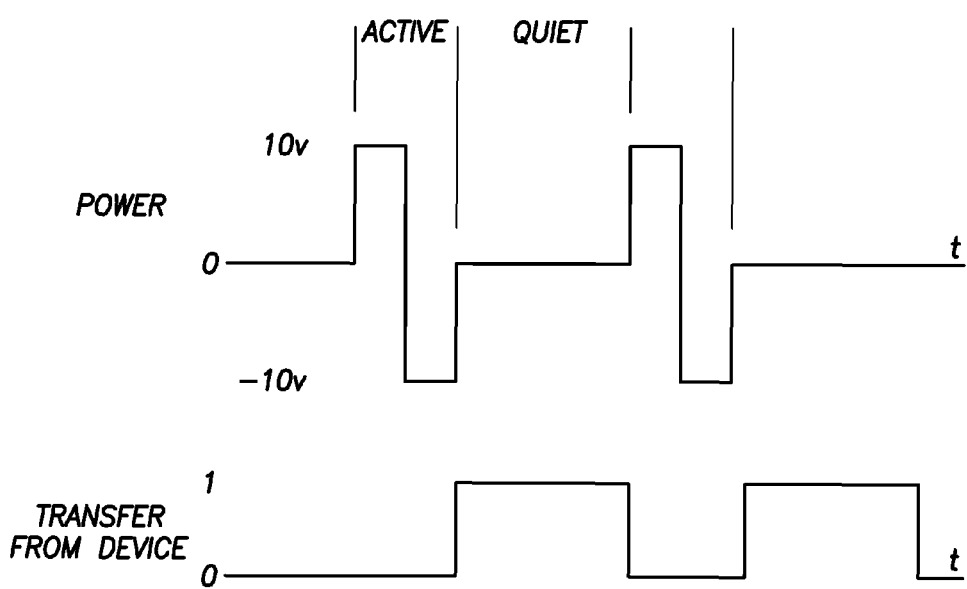

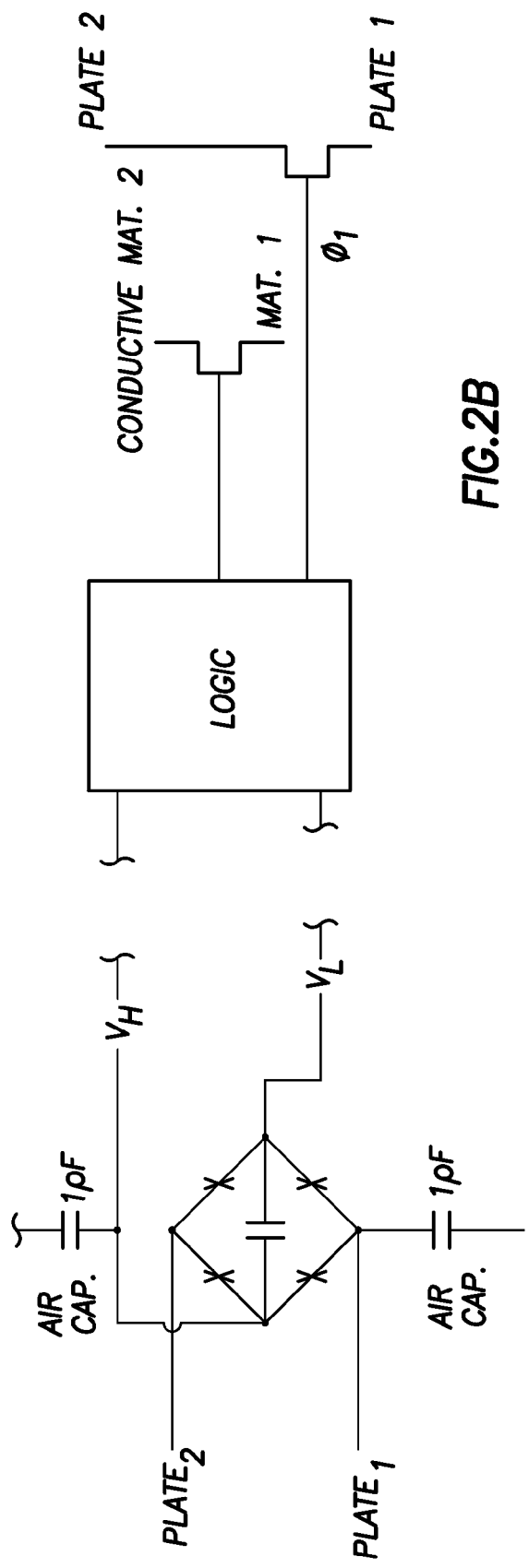

SYSTEM FOR SUPPLY CHAIN MANAGEMENT

CROSS-REFERENCE TO RELATED APPLICATIONS

This application is a continuation of U.S. patent application Ser. No. 13/508,327 filed on May 4, 2012, now U.S. Pat. No. 8,868,453, which is the U.S. National Stage entry of International Application No. PCT/US2010/055522, filed on Nov. 4, 2010, which claims priority under 35 USC 119 from U.S. Provisional Application Ser. No. 61/258,182 filed on Nov. 4, 2009 titled "METHOD, DEVICE AND SYSTEM FOR SUPPLY CHAIN MANAGEMENT OF INGESTIBLE EVENT MARKERS" by inventor Mark Zdeblick, all of which are incorporated herein in their entirety.

FIELD OF THE INVENTION

The present invention is related to methods and systems for using electronic devices to track products. More specifically, the present disclosure includes a methods, devices, and system for tracking medical inventory from source to consumer.

BACKGROUND

Suppliers of pharmaceutical products are concerned about counterfeit products being substituted for original products from the time the products leave the manufacturer to the time the products are delivered to the end user. Additionally, there is a need for accurately determining the quantity and content of a package so that the distributors can identify the products throughout the supply chain. Known methods and systems use near field communication, such as RFID. These known methods have inherent limitations such as lack of data integrity, confidentiality etc. Therefore, what is needed is a system for interrogating a product to ensure validity and origin of the product throughout the supply chain, from manufacturer to end user or consumer.

SUMMARY

Disclosed is a system to manage product supply in a supply chain environment. In various aspects, the invention includes capacitive plates which probe a variety of products, resulting in indications of product validity or invalidity. In this manner, various supply chain or other pursuits may be accomplished.

The products include, for example, IV bags, syringes, ingestible event markers (IEMs) and similar devices, as disclosed and described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO 2009/042812; PCT application serial no. PCT/US09/53721; and PCT application serial no. PCT/US2007/015547 published as WO 2008/008281; as well as U.S. Provisional Application Ser. Nos. 61/142,849; 61/142,861; 61/177,611; 61/173,564; each in its entirety is incorporated herein by reference. Such products may typically be designed to include conductive materials/components. The use of capacitive coupling to probe the product's conductive materials and components by the capacitive plates may indicate the presence of the correct configuration of conductive components of the product. Alternatively, failure to communicatively couple when probed may indicate product nonconformance, e.g., one or more conductive materials is absent, incorrectly configured, etc.

BRIEF DESCRIPTION OF THE DRAWINGS

FIG. 1A shows a pharmaceutical product with a device that can be interrogated using capacitive coupling in accordance with one aspect of the present invention.

FIG. 1B shows a pharmaceutical product with a device that can be interrogated using capacitive coupling in accordance with another aspect of the present invention.

FIG. 1E shows a pharmaceutical product with a device that can be probed or interrogated with a co-axial probe/plates using capacitive coupling in accordance with yet another aspect of the present invention.

FIG. 2A shows a diode bridge use in the device of FIG. 2.

FIG. 2B shows a logic unit of the device of FIG. 2 in communication with a probe through the plates and the conduction material, which is associated with the device in accordance with the present invention.

FIG. 2C shows a finite time period for a power transfer cycle and an information transfer cycle using capacitive coupling in accordance with the teachings of the present invention.

DETAILED DESCRIPTION

Figure 1C:
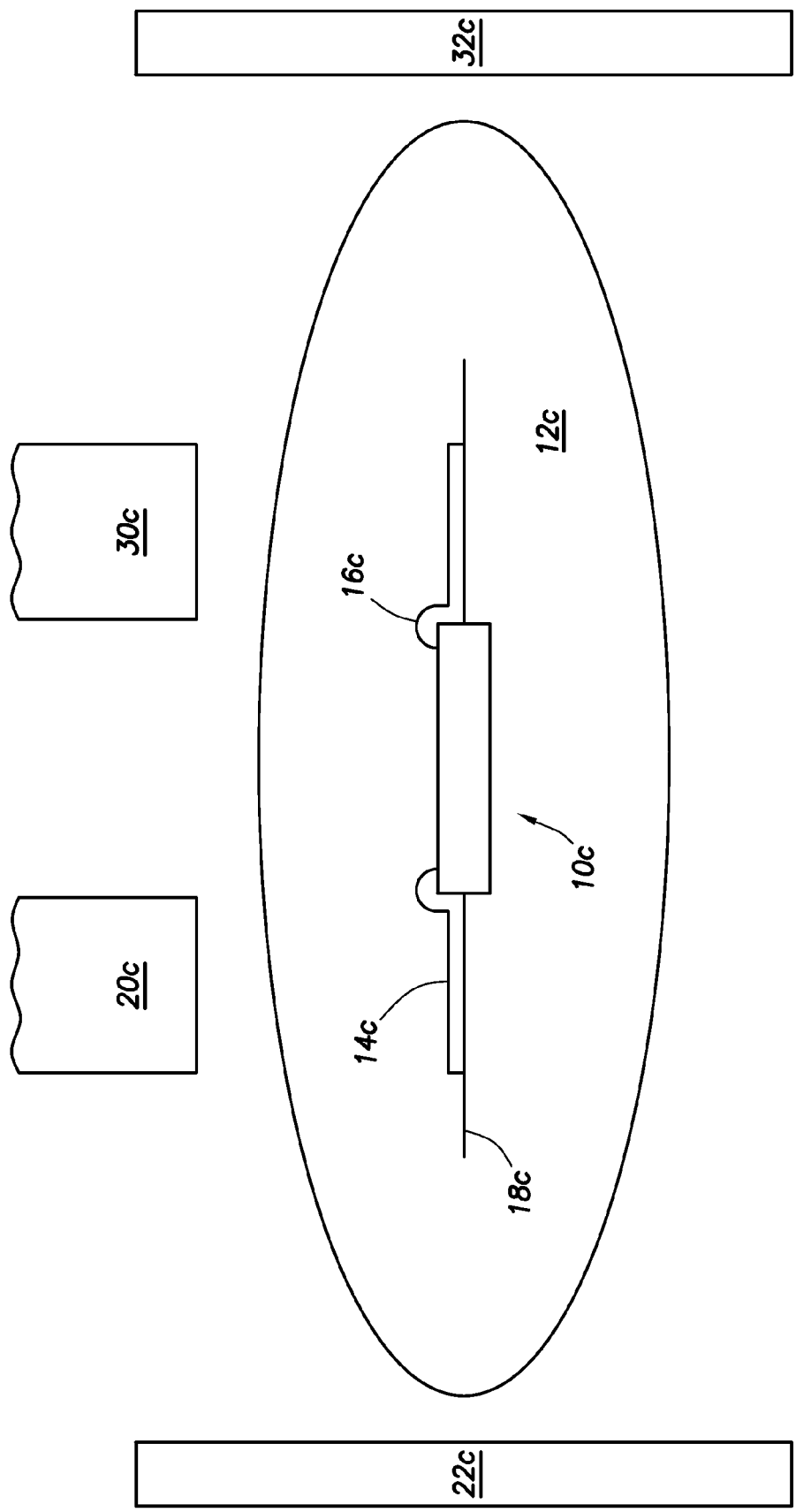
FIG. 1C shows a pharmaceutical product with a device that can be interrogated using capacitive coupling in accordance with another aspect of the present invention.

Referring now to FIG. 1A, a device 10a inside a pharmaceutical product 12a, such as a pill or tablet, which is completely packaged up and tested via a probe, as discussed in detail below. In accordance with various aspects of the present invention, the device 10a may be located within the product 12a or secured to the surface of the product 12a, as contemplated within the scope of the present invention. The device 10a includes a control module for communication and a memory for storing information, such as identity. The probing of the device 10a is performed to ensure, for example, that the device 10a is still functioning. The probing uses a capacitive coupling approach where there is capacitive coupling of a first probing capacitive plate 20a to a first metal or material 14a on one side of the device 10a and a second probing capacitive plate 30a to a second metal or material 16a on another side of the device 10a. As evident to one skilled in the art, the plate 20a is electrically insulated from the plate 30a even though the insulation is not specifically shown. Various ways to probe using capacitive coupling may be accomplished, e.g., metal, metal pads, etc. In accordance with one aspect of the present invention, for example, there is capacitive coupling between material 14a and capacitive plate 20a and material 16a and capacitive plate 30a. The plates 20a and 30a are probes that can communicate with the device 10a through capacitive coupling. The plates 20a and 30a are electrically connected to a system (not shown) that can receive the information from the plates 20a and 30a as well as process the information. Also, in accordance with various aspects of the present invention, the product may be coated with non-conducting material.

In accordance with various aspects of the present invention, there are various components included as part of the device 10. For example, the device 10 may be an ingestible event marker (IEM) with a unique identity that can be read using capacitive coupling pre-ingenstion and communicated using transconduction post-consumption. Various aspects of an IEM are disclosed in U.S. patent application Ser. No. 12/564,017 titled COMMUNICATION SYSTEM WITH PARTIAL POWER SOURCE filed on Sep. 21, 2009, the entire disclosure of which is incorporated herein by reference.

Referring now to FIG. 1B, a device 10b is shown as part of a product 12b in accordance with one aspect of the present invention. The device 10b includes a first material 14b and a second material 16b deposited on the surface of the device 10b for forming a capacitive connection. The materials 14b and 16b are in communication with the control module of the device 10b. Probes 20b and 30b are capacitively coupled to materials 14b and 16b, respectively. Thus, as the probes 20b and 30b are powered up with AC voltage, then materials 14b and 16b are capacitively coupled to the probes 20b and 30b. Thus, information associated with the device 10b that is stored in the memory of the device 10b can be encoded by a control module of the device 10b and communicated to the probes using capacitive coupling.

Referring now to FIG. 1C, a device 10c is shown secured to a product 12c in accordance with the present invention. The device 10c includes a first material 14c and a second material 16c deposited around the perimeter of a skirt 18c of the device 10c with at least a portion of the materials 14c and 16c being deposited on the skirt 18c. Furthermore, the materials 14c and 16c are coupled to the control module of the device 10c to allow for communication through capacitive coupling from the control module of the device 10c to allow the identity of the device 10c to be communicated to a system through the probes 20c and 30c. In accordance with one aspect of the present invention, the materials 14c and 16c are conductive inks, such as an ingestible graphite or carbon based ink or paste. Probes 20c and 30c are powered by an AC source and when brought close to the materials 14c and 16c, the probes 20c and 30c can communicate with the device 10c using capacitive coupling through the materials 14c and 16c, respectively. Furthermore, in accordance with another aspect of the present invention, probes 22c and 32c are positioned proximal to the material 14c and 16c at different locations to allow for alternative positioning of the device 10c or to provide for probing of the device from an alternative direction. Once the probes 20c and 30c are powered with an AC voltage and the device 10c is located near the probes 20c and 30c, then the materials 14c and 16c can be used to pass information between the device 10c and the system connected to the probes 20c and 30c through capacitive coupling.

Figure 1D:
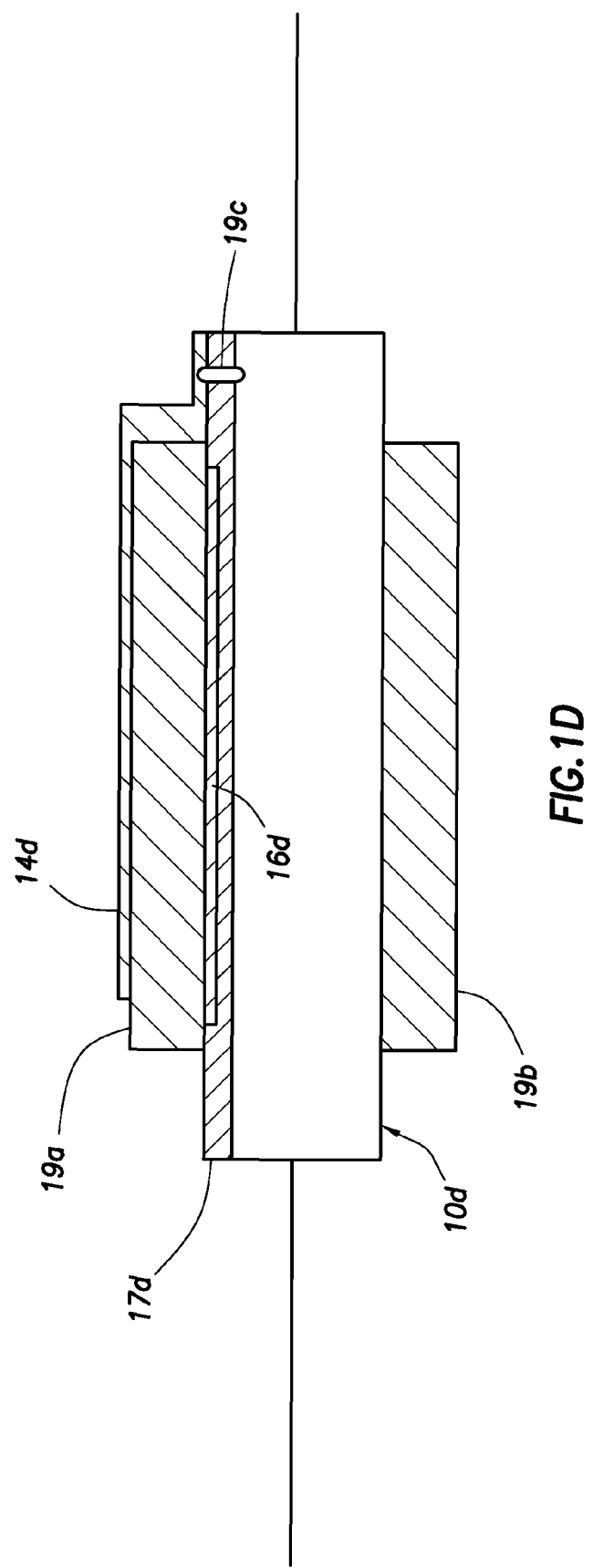
FIG. 1D shows a device that can be probed or interrogated using capacitive coupling in accordance with yet another aspect of the present invention.

Referring now to FIG. 1D, a device 10d is shown in accordance with another aspect of the present invention. A conducting material 14d is deposited on the surface of a material 19a that is associated with the device 10d. The material 19a and the material 19b of the device 10d are dissimilar materials and form a partial power source for the device 10d. For example, the material 19a maybe CuCl and the material 19b may be Mg. The device 10d also includes transistors at connection 19c that is capable of electrically connected the composite 14d to V-high or the material 19b, which is at the same potential as V-low. The device 10d includes a composite material 16d that is physically associated with the device 10d and rests on top of an oxide layer 17d. The material 16d may be gold-plated CuCl. Thus, as probes or plates, similar to those shown in FIGS. 1A-1C and powered by an oscillating or AC voltage source, are brought close to the device 10d there is capacitive coupling between the composite 14d and the composite 16d and the probes. In accordance with one aspect of the present invention, as the voltage source isolates, the energy transferred to the material 14d and the material 16d varies accordingly and is stored on the device 10d. As the voltage source is reduce to zero or quiet, then the device 10d switches from receiving energy to sending energy to the probes using capacitive coupling. In order to creating an oscillating energy source, the transistors 19c are used to connect and disconnect the material 14d between the material 19b (which represents V-low) and V-high. As the material 14d changes energy levels from V-high to V-low, information can be transferred to the probes. Thus, during a portion of the cycle when the power is off or quiet (as shown in FIG. 2C), the device 10d is able to transfer energy to the probes, which energy includes information about the device 10d. Hence, using capacitive coupling, information may be communicated between the device 10d and the system connected to the probes near the device 10d.

Referring now to FIG. 1E, a co-axial probe with two conductive probes/plates 20e and 30e separated by an insulating material 25e. The inner conductive probe or plate 20e is surrounded by the insulating material 25e, which is surrounded by the outer conductive probe or plate 30e. The device 10e is shown as part of a pharmaceutical product 12e. The device 10e includes a conducting material or ink 15e deposited on the side opposite the co-axial probe. As the co-axial probe is positioned close to the product 12e, the probe 20e is positioned over the center of the device 10e and the probe 30e is positioned above the outer edges of the device 10e and proximal to the material 15e. Thus, as described above and with respect to FIG. 2C, as the power source is isolating, energy is transferred from the co-axial probe to the device 10e and as the power source is shut-off or quiet, then energy is transferred from the device 10e to the system connected to the co-axial probe.

Figure 2:
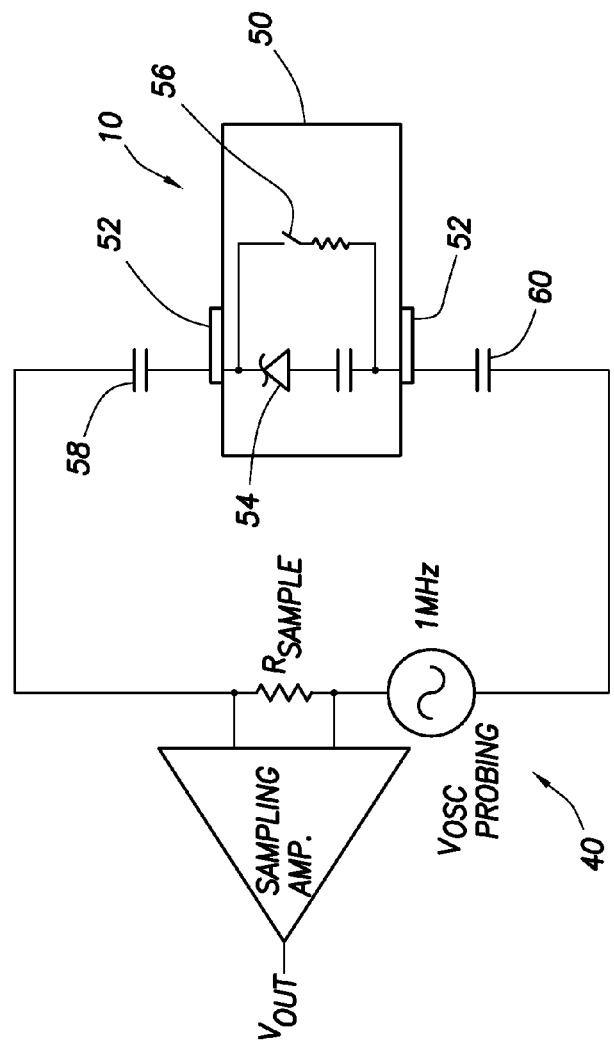
FIG. 2 shows a circuit diagram for the device of FIGS. 1A-1D in accordance with one aspect of the present invention.

Referring now to FIG. 2, a voltage source, e.g., an AC voltage or other isolating or alternating source 40 runs at a high frequency, e.g., 1 MHz, etc. The voltage source is connected to the probes or plates. The device 10 includes a control module 50 and bonding pads 52 to which the materials (for example, materials 14 and 16 of FIG. 1A) are coupled. In accordance with one aspect of the present invention, inside the device 10 is a diode 54, such as a Schottky diode or other type of diode that creates an internal supply voltage, and a switch 56 with some impedance that is turned on and off which changes the impedance of the device 10. The variation in the impedance is used to communicate information about the identity of the device 10. The change in impedance allows for the information associated with the device 10 to be encoded and sent to a system through the probes using capacity coupling, as represented by the capacitors 58 and 60. The information is captured by the system connected to the probes represented by the capacitors and read as Vout through the sampling amplifier across the impedance labeled R-sample.

Once the control module 50 is brought near or exposed to the voltage source through the plates, there is energy transfer through the capacitive coupling and the device 10 can produce an oscillation signal, which can be detected. The oscillation signal contains information and the isolating signal can be encoded into, for example, a 1 MHz signal or similar frequency, e.g., 500 KHz, as may be dependent on the degree of capacitive coupling. The voltage of the source 40 will be determined by how much capacitive coupling is achieved between the capacitive plate or probe 20 and 30 of FIG. 1 and the materials 14 and 16 thereof. Thus, at a high frequency that represents, perhaps, 5 volts, the capacitive value between the probe, such as probe 20 or 30, and the material is represented by the capacitors 58 and 60.

Referring now to FIGS. 2A and 2B, in accordance with another aspect of the present invention, a diode bridge is shown that is a circuit representation of the interaction between the plates 20 and 30 and the materials 14 and 16 of the device 10. The isolating voltage present at the plates 20 and 30 (labeled "PLATE 1" and "PLATE 2") results in an energy transfer in the form of high voltage and a low voltage for the device 10. The device 10 includes a control module as part of the processor or logic unit. The logic unit may be a processor, a microprocessor, a multi-module device or any form of integrated circuit. The logic unit is in communication with the conductive materials 14 and 16 and the plates 20 and 30 (labeled "PLATE 1" and "PLATE 2"). As the plates 20 and 30 are powered with an AC source, the logic unit stores energy and later uses that energy to send information.

Referring now to FIG. 2C, the power cycle is shown with an active period and a quiet period and the transfer cycle of the device 10 is shown as the transfer window. In accordance with the present invention, the duration of the active period energy is transferred from the power source to the device 10. Then during the quiet phase, the energy stored by the device 10 is used to transfer energy from the device 10 to the system connected to the probes. In this way, information associated with the device can be transferred from the device 10 through the probes 20 and 30 to the system connected to the probes. In accordance with various aspects of the present invention, the information sent from the device 10 to the system of the probes 20 and 30 during the quiet phase is based on the information stored in memory of the device. Thus, even though there is a "1" shown during the transfer window or quiet stage of the power source, the information transferred during the quiet stage or phase of the power source may be a "0".

In accordance with one aspect of the present invention, if there is a one-microfarad capacitor between a capacitive plate/probe and a material physically associated with the device 10, then at a high isolating frequency that represents a lower voltage necessary for capacitive coupling. In accordance with another aspect of the present invention, if there is a one-picofarad capacitor, then a larger voltage may be needed, as will be recognized by one skilled in the art. The amount of current actually going through will depend on the impedance between the electrical circuit caused between the capacitive plates/probes 20 and 30, as shown in FIG. 1 for example. Thus shorting capacitive plate 20 and capacitive plate 30 of FIGS. 1A-1C will result in significant current going through which may be detected with, for example, by a sampling amplifier as shown in FIG. 2. The output is through a sampling amplifier which is essentially looking at the current going through the loop and the modulation of that current caused by the control module 50.

In accordance to various aspects of the present invention, the capacitive coupling may be used with devices that are DC source devices, which are modified for interoperability, e.g., a device having a rectifier in place to provide a stable voltage on the chip, the impedance of which may be modulated.

Figure 3A:
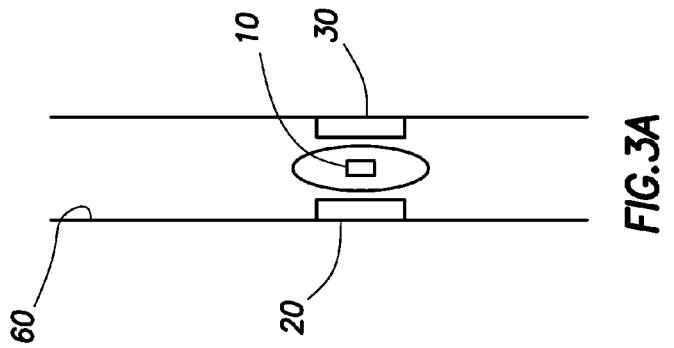
FIG. 3A shows a product with the device passing through a tubular section to confirm product authenticity and device operation in accordance with the present invention.
Figure 3B:
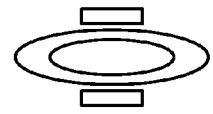
FIG. 3B is a specific instant of the device passing between plates during interrogation to confirm authenticity of the product in accordance with the present invention.

Referring now to FIGS. 3A and 3B, in accordance with various aspects of the present invention, the capacitive plates/probes and the system connected thereto for receiving information may be integrated or otherwise associated with various structural components and other devices, e.g., a tubular structure 60 as shown in FIG. 3A having capacitive plates 20 and 30. To illustrate, one or more pharmaceuticals having an IEM or similar device 10 may be introduced into the structure. The device 10 may be introduced manually or automatically via automated means. As the device travels through the structure 60, the device 10 is probed by the capacitive plates 20 and 30 in the tube 60. In various aspects, other devices and/or components may be associated. In one example, a programmable device may be communicatively associated with the capacitive coupling device to receive and/or transmit data and/or information derived by the capacitive coupling device. To continue with the foregoing illustration, once all or a portion of the number of products 10, which may be pills, are probed or "read" by the capacitive coupling system associated with the probes/plates 20 and 30, the capacitive coupling system can communicate, e.g., wireless, wired, etc., to a database with a display device for further storage, display, manipulation, etc. In this manner, an individual datum, data, large volumes of data, etc., may be processed for various purposes. One such purpose may be, for example, to track pharmaceuticals in a supply chain application, e.g., during a manufacturing process such as a tablet pressing or other process, during a pharmacy verification process, during a pharmacy prescription process, etc. Various processes may be complementary, incorporated, etc. One such example is validation through reading the number. If it is valid, e.g., readable, the tablet is accepted. If not, the tablet is rejected. Thus, using a simple hand held reader with an oscillating power source, a user or care provider can probe the product, which can be a pill or tablet in accordance with one aspect of the present invention, with the device 10 associated therewith and determine if the pill is authentic or a counterfeit product.

Figures 4A, 4B:
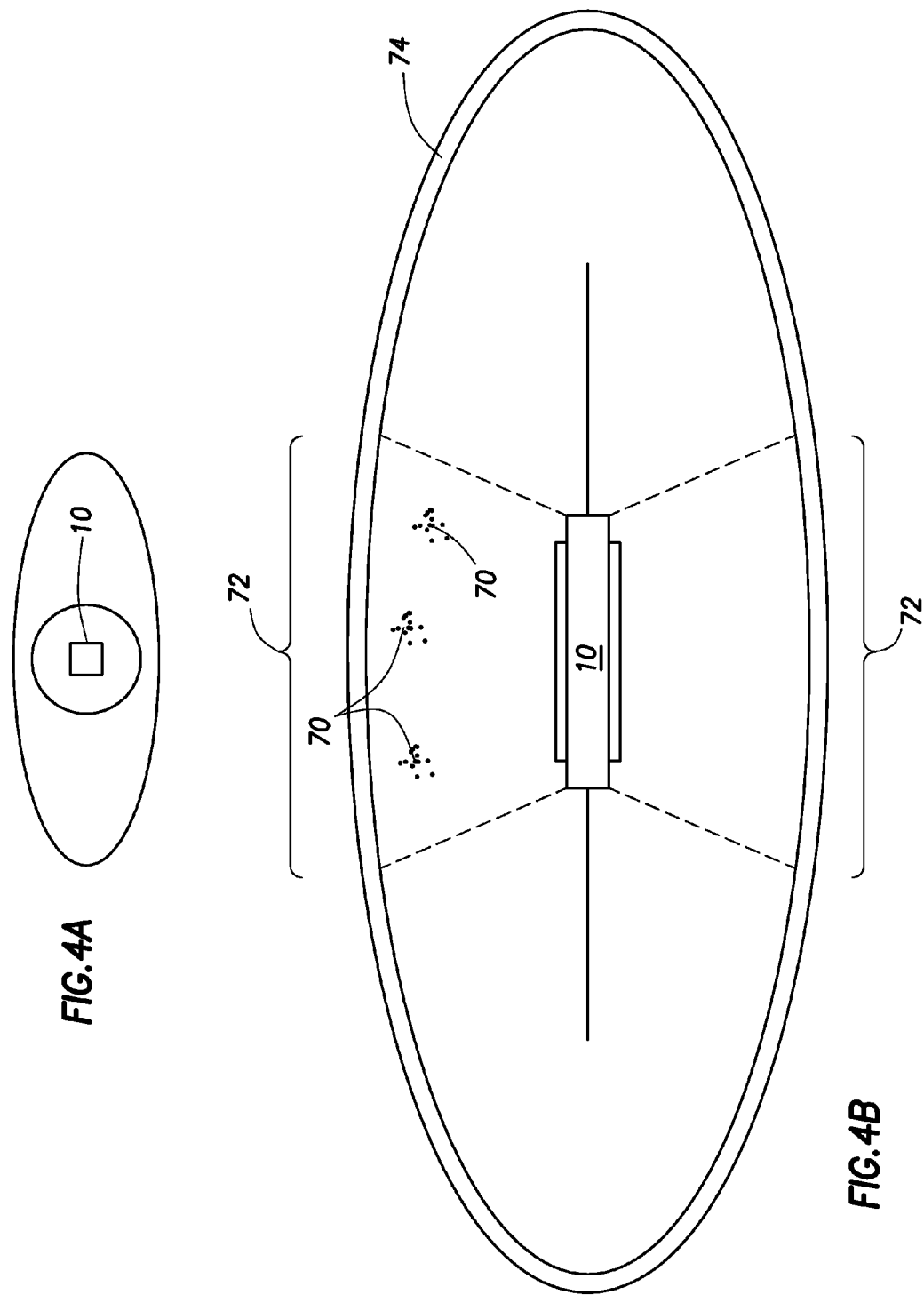
FIG. 4A is a top view of the device associated with a product in accordance with the present invention.
FIG. 4B is a side view of a product with a conducting composite and the device in accordance with the present invention.

Referring now to FIGS. 4A and 4B, in accordance with another aspect of the present invention, a pill having a device 10 is shown with a coating 74 that is non-conductive or fairly impervious coating and the pill itself comprises a non-conductive medicine powder. A region 72, e.g., a cone-shaped region, as shown, comprises a conductive material 70, e.g., small particles or grains of conductive material intermixed with other pharmaceutical material(s), excipient(s), placebo material(s), etc., such that the region 72 is converted into a conductive region. For example, graphite and other conductive materials may be used, e.g., one part in ten, five parts in ten, etc. such that the region 72 is conductive. Other materials and compositions are possible, e.g., a gel or liquid capsule having conductive particles therein, etc. Thus, at high enough frequencies, the particles of the conductive material 70 in the region 72 may be shorted together. One skilled in the art will recognize that the conductive material 70 may include various materials and form factors, as well as combinations thereof, e.g., variously sized particles, wires, metal films, threads, etc. The scope of the present invention is not limited by the type or shape of the conductive material 70 used in the region 72.

In accordance with another aspect of the present invention, the conductive material 70 may be integrated or formed via a variety of methods and proportions. In one example, the device 10 is embedded or otherwise mechanically associated with a "doughnut-shaped" powder and the hole formed therein is filled or otherwise associated with the conductive particles, etc., to form the conductive region. The size, area, volume, locations or other parameters of the conductive regions may vary to the extent the functionality described herein may be carried out.

Figure 5:
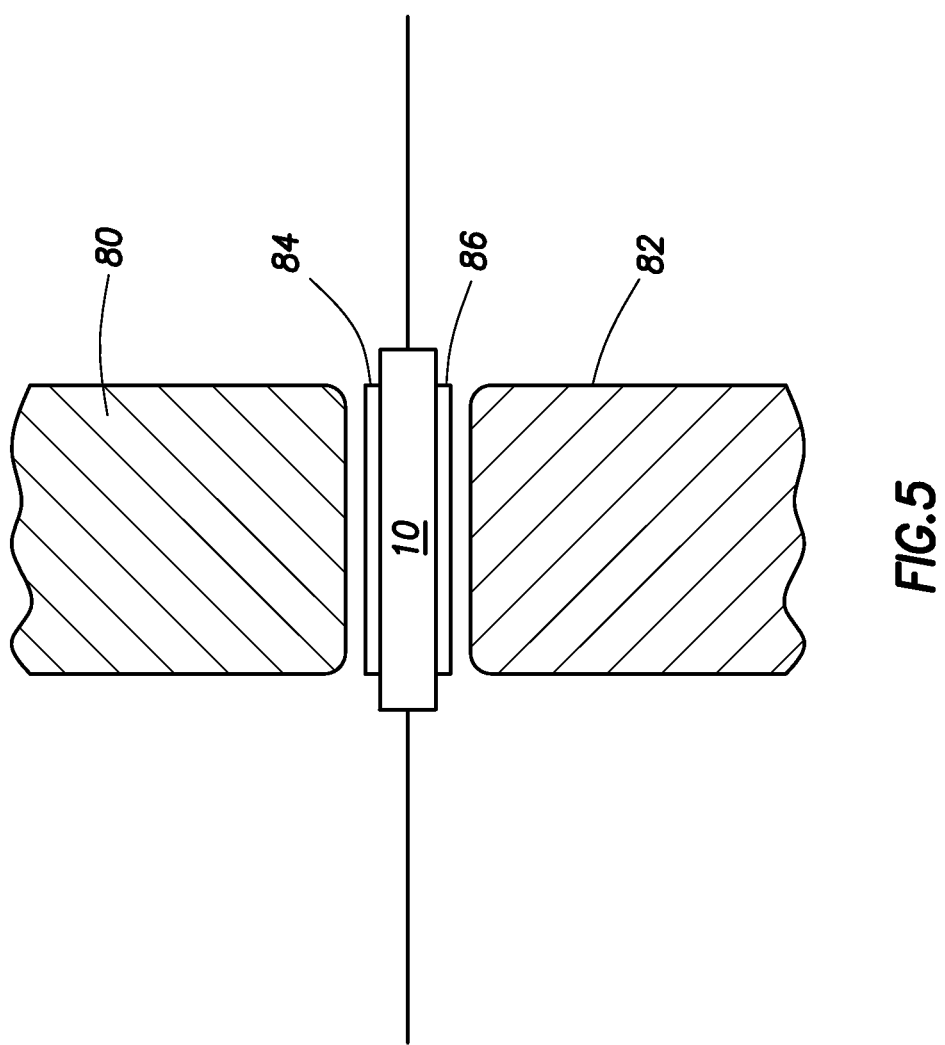
FIG. 5 shows a side view of a device being interrogated by a pair of probes in accordance with the present invention.

In accordance with another aspect of the present invention and as shown in FIG. 5, capacitive plates or probes 80 and 82 are coupled to a system for collecting the data. Probes 80 and 82 are used to probe the device 10 through capacitive coupling to the materials 84 and 86, respectively. An impedance feedback system may be used to drive them fairly close to one another and once the current gets to a certain amount to use that to gauge the distance. Using a high enough impedance, this system may be useful in a variety of applications, e.g., a manufacturing environment to validate that the device 10 is present, is operating correctly etc.

In accordance with another aspect of the present invention, a close proximity between the capacitive coupling probes/plates and the device 10 may facilitate, promote, etc., privacy aspects. In certain aspects, certain related devices may include, for example, a circuit with a Schottky diode in parallel with a CMOS transistor that is timed to be opened and closed, opened up, etc. Other circuit designs and modifications are possible.

What is claimed is:

1. An ingestible device configured to be tested using a probe located external from the ingestible device, the ingestible device comprising:
    a substrate comprising a control unit and a memory for storing information; and
    first and second materials physically associated with the substrate, the first material configured to be capacitively coupled to a first plate of a probe located external from the ingestible device and the second material is configured to be capacitively coupled to a second plate of the probe such that information can be communicated between the first material and the first plate and between the second material and the second plate;
    wherein the first and second materials are configured to energize the ingestible device by a transfer of energy from the first and second plates to the corresponding first and second materials to validate the functionality of the ingestible device.

2. The ingestible device of claim 1, wherein the first and second materials are communicably coupled to the control unit.

3. The ingestible device of claim 1, further comprising a region of conductive material physically associated with the substrate.

4. The ingestible device of claim 3, wherein the region of conductive material comprises a mixture of particles of a conductive material and at least one other material.

5. The ingestible device of claim 4, wherein the at least one other material comprises at least one pharmaceutical material, at least one excipient, or at least one placebo material.

6. The ingestible device of claim 1, wherein the first material comprises a material dissimilar from a material of the second material.

7. The ingestible device of claim 6, wherein the first and second materials are configured to provide a voltage potential difference when the dissimilar materials of the first material and the second material are in contact with an electrically conductive liquid and wherein the control unit is configured to alter a conductance between the first and second materials such that a current is varied to encode information in a signal communicated by the electrically conductive liquid such that the encoded information can be remotely detectable by a receiver.

8. The ingestible device of claim 1, further comprising an antenna coupled to the control unit, the antenna configured to communicate with an external device.

9. The ingestible device of claim 8, wherein the antenna includes a coil.

10. A system for tracking, from an origin to a destination, an ingestible device configured to be tested using a probe located external from the ingestible device, the system comprising:
    a probe comprising:
        a power source;
        a processor coupled to the power source configured to receive and send information;
        a first plate coupled to the processor; and
        a second plate coupled to the processor, wherein the power source is configured to be controlled by the processor to produce an output at the first and the second plates; and
    an ingestible device comprising:
        a substrate comprising a control unit and a memory for storing information; and
        first and second materials physically associated with the substrate, the first material configured to be capacitively coupled to the first plate of the probe located external from the ingestible device and the second material is configured to be capacitively coupled to the second plate of the probe such that information can be communicated between the first material and the first plate and between the second material and the second plate;
        wherein the first and second materials are configured to energize the ingestible device by a transfer of energy from the first and second plates to the corresponding first and second materials to validate the functionality of the ingestible device.

11. The system of claim 10, wherein the first plate has a surface facing a surface of the second plate such that the ingestible device is configured to be in capacitive communication with the probe when the ingestible device is positioned between the surfaces of the first and second plates.

12. The system of claim 10, wherein the first plate is positioned adjacent the second plate such that the ingestible device is configured to be in capacitive communication with the probe when the ingestible device is brought within an operative proximity of the probe.

13. The system of claim 10, wherein the probe further comprises a tube having the first and second plates contained therein.

14. The system of claim 10, wherein the first and second materials are configured to be communicably coupled to the control unit.

15. The system of claim 10, wherein the ingestible device comprises a region of conductive material physically associated with the substrate.

16. The system of claim 15, wherein the region of conductive material comprises a mixture of materials, wherein at least a portion of the mixture of materials is a conductive material.

17. The system of claim 16, wherein the mixture of materials comprises a conducting ink.

18. The system of claim 10, wherein the ingestible device is configured to communicate with an external device.

19. The system of claim 18, wherein the ingestible device comprises a communication element configured to communicate with the external device, the communication element including at least one of:

an antenna, or the first material and the second material different from the first material, wherein the first material and the second material are selected to provide a voltage potential difference as a result of the different materials being in contact with an electrically conductive liquid, and wherein the control unit is configured to alter a conductance between the first and second materials such that a current is varied to encode information in a signal communicated by the electrically conductive liquid to produce encoded information such that the encoded information is remotely detectable by a receiver.

* * * * *